United States Patent [19]

Teall et al.

[11] Patent Number: 5,633,281

[45] Date of Patent: May 27, 1997

[54] 3,3-DIPHENYL PROP-2-YL AMINO ACID DERIVATIVES AND THEIR USE AS TACHYKININ ANTAGONISTS

[75] Inventors: Martin R. Teall, Stanstead; Brian J. Williams, Great Dunmow, both of United Kingdom

[73] Assignee: Merck Sharp & Dohme Ltd., Hoddesdon, England

[21] Appl. No.: 492,067

[22] PCT Filed: Dec. 17, 1993

[86] PCT No.: PCT/GB93/02592

§ 371 Date: Dec. 8, 1995

§ 102(e) Date: Dec. 8, 1995

[87] PCT Pub. No.: WO94/15903

PCT Pub. Date: Jul. 21, 1994

[30] Foreign Application Priority Data

Jan. 4, 1993 [GB] United Kingdom ............... 9300051

[51] Int. Cl.⁶ ................................. A61K 31/195
[52] U.S. Cl. ............................. 514/567; 562/444
[58] Field of Search ........................ 562/444; 514/567

[56] References Cited

FOREIGN PATENT DOCUMENTS

| 0394989A3 | 4/1990 | European Pat. Off. . |
| 0436334A3 | 12/1990 | European Pat. Off. . |
| 0499313A1 | 2/1992 | European Pat. Off. . |
| 2035535 | 7/1969 | Germany . |
| WO93/01160 | 3/1992 | WIPO . |

OTHER PUBLICATIONS

Dec. 17, 1995 PCT Search Report.
Morrison et al, "Organic Chemistry", p. 673 (1966).

*Primary Examiner*—James H. Reamer
*Attorney, Agent, or Firm*—Robert J. North; Melvin Winokur

[57] ABSTRACT

Compounds of formula (I), or a salt or prodrug thereof, wherein $R^1$ represents H, $C_{1-4}$ alkyl or $CH_2COOH$; $R^2$ represents H or $C_{1-4}$ alkyl, with the proviso that $R^1$ and $R^2$ are not both H; $R^3$ and $R^4$ each independently rely resent H, $C_{1-}$, alkyl. $C_{2-6}$ alkenyl $C_{1-6}$ alkoxy, halo or trifluoromethyl; $A^1$, $A^2$, $A^3$, and $A^4$ each independently represent H, $C_{1-6}$ alkyl, $C_{1-6}$ alkenyl, $C_{1-6}$ alkoxy, halo or trifluoromethyl; and $A^5$ and $A^6$ each independently represent H or $C_{1-4}$ are tachykinin antagonists useful

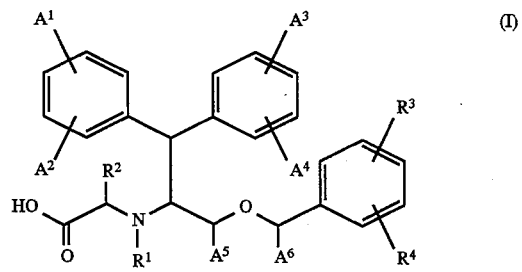

8 Claims, No Drawings

3,3-DIPHENYL PROP-2-YL AMINO ACID DERIVATIVES AND THEIR USE AS TACHYKININ ANTAGONISTS

This application is a 371 PCI/GB93/02592.

This invention relates to a class of aromatic compounds which are useful as tachykinin antagonists. More particularly, the compounds of the invention contain a diphenyl moiety and a substituted amine moiety.

The tachykinins are a group of naturally occurring peptides found widely distributed throughout mammalian tissues, both within the central nervous system and in peripheral nervous and circulatory systems.

The structures of three known mammalian tachykinins-are as follows:
Substance P:
(Arg-Pro-Lys-Pro-Gln-Gln-Phe-Phe-Gly-Leu-Met-NH$_2$
Neurokinin A:
(His-Lys-Thr-Asp-Ser-Phe-Val-Gly-Leu-Met-NH$_2$
Neurokinin B:
Asp-Met-His-Asp-Phe-Phe-Val-Gly-Leu-Met-NH$_2$ For example, substance P is believed inter alia to be involved in the neurotransmission of pain sensations [Otsuka et al, "Role of Substance P as a Sensory Transmitter in Spinal Cord and Sympathetic Ganglia" in 1982 Substance P in the Nervous System, Ciba Foundation Symposium 91, 13–34 (published by Pitman) and Otsuka and Yanagisawa, "Does Substance P Act as a Pain Transmitter?"0 TIPS (December 1987) 8 506–510], specifically in the transmission of pain in migraine (B. E. B. Sandberg et al, J. Med Chem, (1982) 25 1009) and in arthritis [Levine et al in Science (1984) 226 547–549]. These peptides have also been implicated in gastrointestinal (GI) disorders and diseases of the GI tract such as inflammatory bowel disease [Mantyh et al in Neuroscience (1988) 25 (3) 817–37 and D. Regoli in "Trends in Cluster Headache" Ed. Sicuteri et al Elsevier Scientific Publishers, Amsterdam (1987) page 85)]. It is also hypothesised that there is a neurogenic mechanism for arthritis in which substance P may play a role [Kidd et al "A Neurogenic Mechanism for Symmetrical Arthritis" in The Lancet, 11 Nov. 1989 and Grönblad et al "Neuropeptides in Synovium of Patients with Rheumatoid Arthritis and Osteoarthritis" in J. Rheumatol. (1988) 15(12) 1807–10]. Therefore, substance P is believed to be involved in the inflammatory response in diseases such as rheumatoid arthritis and osteoarthritis, and fibrositis [O'Byrne et al in Arthritis and Rheumatism (1990) 33 1023–8]. Other disease areas where tachykinin antagonists are believed to be useful are allergic conditions [Hamelet et al Can. J. Pharmacol. Physiol. (1988) 66 1361–7], immunoregulation [Lotz et al Science (1988) 241 1218–21 and Kimball et al, J. Immunol. (1988) 141 (10) 3564–9] vasodilation, bronchospasm, reflex or neuronal control of the viscera [Mantyh et al, PNAS (1988) 85 3235–9] and, possibly by arresting or slowing β-amyloid-mediated neurodegenerative changes [Yankner et al Science (1990) 250, 279–82] in senile dementia of the Alzheimer type, Alzheimer's disease and Downs Syndrome. Substance P may also play a role in demyelinating diseases such as multiple sclerosis and amyotrophic lateral sclerosis [J. Luber-Narod et. al., poster to be presented at C.I.N.P. XVIIIth Congress, 28th Jun.-2nd Jul., 1992], and in disorders of bladder function such as bladder detrusor hyper-reflexia (Lancet, 16th May, 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosis (European patent application no. 0 436 334), opthalmic disease such as conjuctivitis, vernal conjunctivitis, and the like, and cutaneous diseases such as contact dermatitis, atropic dermatitis, urticaria, and other eczematoid dermatitis (European patent application no. 0 394 989).

We have now found a class of non-peptides which are potent antagonists of tachykinin.

The present invention provides a compound of formula (I), or a salt or prodrug thereof:

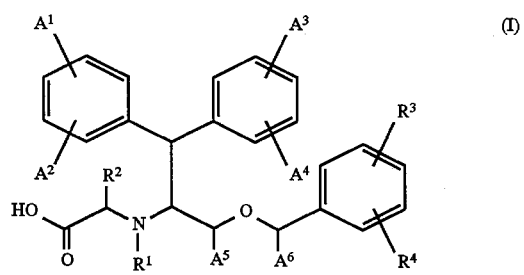

wherein

R$^1$ represents H, C$_{1-4}$alkyl or CH$_2$COOH;

R$^2$ represents H or C$_{1-4}$alkyl, with the proviso that R$^1$ and R$^2$ are not both H;

R$^3$ and R$^4$ each independently represent H, C$_{1-6}$alkyl, C$_{2-6}$alkenyl, C$_{1-6}$alkoxy, halo or trifluoromethyl;

A$^1$, A$^2$ A$^3$ and A$^4$ each independently represent H, C$_{1-6}$ alkyl, C$_{1-6}$ alkenyl, C$_{1-6}$ alkoxy, halo or trifluoromethyl and A$^5$ and A$^6$ each independently represent H or C$_{1-4}$ alkyl.

The alkyl groups referred to with respect to any of the formulae herein may represent straight, branched or cyclic groups. Thus, for example, suitable alkyl groups include methyl, ethyl, n- or iso-propyl, n-, sec-, iso- or tert-butyl, cyclopropyl, cyclobutyl, cyclopentyl or cyclohexyl, and cycloalkyl-alkyl groups such as cyclopropylmethyl.

The term "halo" as used herein includes fluoro, chloro, bromo and iodo, preferably chloro.

Preferably R$^1$ represents H, methyl, ethyl or CH$_2$COOH, more preferably methyl.

Preferably R$^2$ represents H or methyl, more preferably H.

Preferably R$^3$ and R$^4$ are selected from methyl, ethyl, t-butyl, chloro, bromo and trifluoromethyl, more preferably methyl and trifluoromethyl. Preferred are compounds wherein R$^3$ and R$^4$ are located at the 3- and 5-positions of the phenyl ring.

Favourably A$^1$, A$^2$, A$^3$ and A$^4$ each independently represent H, F, Ce, Br, CF$_3$, CH$_3$ or OCH$_3$.

A represents H or F, A$^2$ represents H, A$^3$ represents H or F and A$^4$ represents H.

Preferably A$^1$, A$^2$, A$^3$ and A$^4$ each represent H.

Aptly A$^5$ and A$^6$ each independently represent H or CH$_3$. Favourably A$^5$ and A$^6$ both represent H.

A preferred subgroup of compounds according to the invention is represented by compounds of formula (IA) and salts and prodrugs thereof:

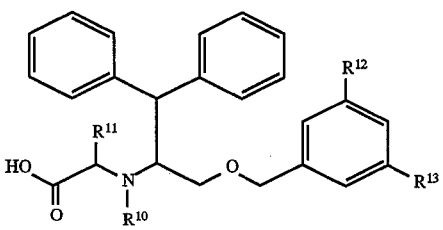

(IA)

wherein $R^{10}$ represents H, methyl or $CH_2COOH$;

$R^{11}$ represents H, methyl or ethyl, with the proviso that when $R^{10}$ is H, $R^{11}$ is not H; and $R^{12}$ and $R^{13}$ each independently represent $C_{1-6}$alkyl, such as t-butyl, methyl or ethyl, $C_{2-6}$alkenyl, such as vinyl, $C_{1-6}$alkoxy, such as methoxy, halo, such as chloro or bromo, or trifluoromethyl.

Specific compounds according to the present invention include:

(S)-N-(1-((3,5-bis(trifluoromethyl)phenyl)methyloxy)-3,3-diphenylprop-2-yl)-N-methylglycine;

(S)-N-(1-(((3-t-butyl-5-chloro)phenyl)methyloxy)-3,3-diphenylprop-2-yl)-N-methylglycine;

(S)-N-(1-((3,5-dimethyl)phenyl)methyloxy)-3,3-diphenylprop-2-yl)-N-methylglycine;

(S)-N-(1-(((3-chloro-5-methyl)phenyl)methyloxy)-3,3-diphenylprop-2-yl)-N-methylglycine;

(S)-N-(1-(((3-bromo-5-methyl)phenyl)methyloxy)-3,3-diphenylprop-2-yl)-N-methylglycine;

(S)-N-(1-(((3,5-dichlorophenyl)methyloxy)-3,3-diphenylprop-2-yl)-N-methylglycine;

(S)-N-(1-(((3-methyl-5-vinyl)phenyl)methyloxy)-3,3-diphenylprop-2-yl)-N-methylglycine;

(S)-N-(1-(((3-ethyl-5-methyl)phenyl)methyloxy)-3,3-diphenylprop-2-yl)-N-methylglycine;

(S)-N-(1-((3,5-bis(trifluoromethyl)phenyl)methyloxy)-3,3-diphenylprop-2-yl)alanine;

(S)-2-(N,N-bis(carboxymethyl)amino)-1-((3,5-bis(trifluoromethyl)phenyl)methyloxy)-3,3)-diphenylpropane;

(S)-N-(1-(((3-methoxy-5-methyl)phenyl)methyloxy)-3,3-diphenylprop-2-yl)-N-methylglycine;

(S)-N-(1-((3,5-bis(trifluoromethyl)phenyl)methyloxy)-3,3-diphenylprop-2-yl)-N-ethylglycine; and salts and prodrugs thereof.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

Preferred salts of the compounds of formula (I) include the tosylate, oxalate, bisoxalate, iodide, hydrobromide and hydrochloride salts. Particularly preferred are the hydrochloride and hydrobromide salts.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

The present invention includes within its scope solvates of the compounds of formula (I) and salts thereof, for example, hydrates.

The compounds according to the invention have at least one asymmetric centre, and may accordingly exist both as enantiomers and as diastereoisomers. It is to be understood that all such isomers and mixtures thereof are encompassed within the scope of the present invention. Preferably the stereochemistry at the carbon to which the benzhydryl moiety is attached is S.

The present invention further provides pharmaceutical compositions comprising one or more compounds of formula (I), or salts or prodrugs thereof, in association with a pharmaceutically acceptable carrier.

Preferably the compositions according to the invention are in unit dosage forms such as tablets, pills, capsules, powders, granules, sterile parenteral solutions or suspensions, or suppositories, for oral, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

The present invention further provides a process for the preparation of a pharmaceutical composition comprising a compound of formula (I), or a salt or prodrug thereof, which process comprises bringing a compound of formula (I), or a salt or prodrug thereof into association with a pharmaceutically acceptable carrier or excipient.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; neurodegenerative disorders such as dementia, including senile dementia of the Alzheimer type, Alzheimer's disease and Down's syndrome; demyelinating diseases such as MS and ALS and other neuropathological disorders such as peripheral neuropathy, for example diabetic and chemotherapy-induced neuropathy, and postherpetic and other neuralgias; respiratory diseases such as chronic obstructive airways disease, bronchopneumonia, bronchospasm and asthma; cystic fibrosis; inflammatory diseases such as inflammatory bowel disease, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atropic dermatitis, urticaria, and other eczematoid dermatitis; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases, of the GI tract such as disorders associated with the neuronal control of viscera such as ulcerative colitis, Crohn's disease and incontinence; disorders of bladder function such as bladder detrusor hyper-reflexia; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine. For example, the compounds of formula (I) may suitably be used in the treatment of disorders of the central nervous system such as anxiety, psychosis and schizophrenia; neurodegenerative disorders such as senile dementia of the Alzheimer type, Alzheimer's disease and Down's syndrome; respiratory diseases such as bronchospasm and asthma; inflammatory diseases such as inflammatory bowel disease, osteoarthritis and rheumatoid arthritis; adverse immunological reactions such as rejection of transplanted tissues; gastrointestinal (GI) disorders and diseases of the GI tract such as disorders associated with the neuronal control of viscera such as ulcerative colitis, Crohn's disease and incontinence; disorders of blood flow caused by vasodilation; and pain or nociception, for example, that attributable to or associated with any of the foregoing conditions or the transmission of pain in migraine.

The compounds of formula (I) are particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis and especially migraine.

The present invention thus provides a compound of formula (I), or a salt or prodrug thereof, for use in therapy.

The present invention further provides a compound of formula (I), or a salt or prodrug thereof, for use in the manufacture of a medicament for the treatment of physiological disorders associated with an excess of tachykinins, especially substance P. The present invention also provides a method for the treatment or prevention of physiological disorders associated with an excess of tachykinins, especially substance P, which method comprises administration to a patient in need thereof of a tachykinin reducing amount of a compound of formula (I), or a salt or prodrug thereof.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day. For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

The compounds according to the invention may be prepared by saponification of a compound of formula (II)

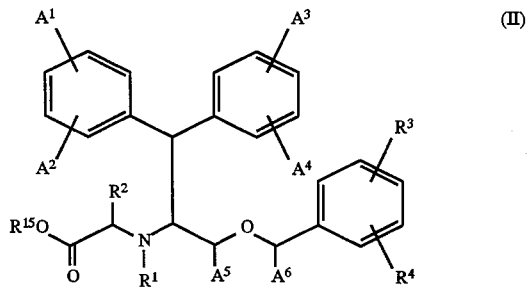

wherein $R^1$, $R^2$, $R^3$, $R^4$, $A^1$, $A^2$, $A^3$, $A^4$, $A^5$ and $A^6$ are as defined for formula (I) above and $R^{15}$ represents $C_{1-6}$alkyl, using conventional methods.

Conveniently the saponification is carried out using an alkali metal hydroxide, such as, for example, sodium hydroxide, in water or an aqueous solvent, suitable at room temperature.

Compounds of formula (II) may be prepared by reaction of compounds of formula (III) with compounds of formula (IV):

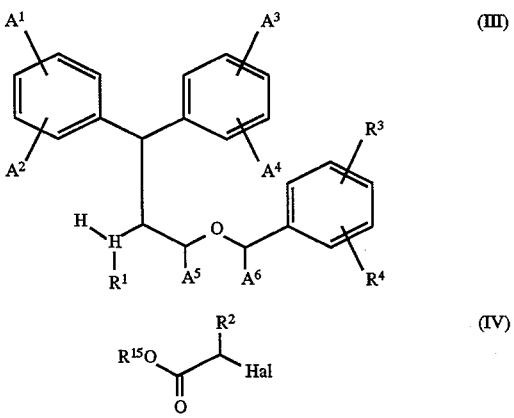

wherein $R^1$, $R^2$, $R^3$, $R^4$, $A^1$, $R^{15}$, $A^2$, $A^3$, $A^4$, $A^5$, and $A^6$ are as previously defined and Hal represents halo such as chloro or, preferably bromo, in the presence of a base.

Suitable bases of use in the reaction include alkali metal hydrides, such as, for example, sodium hydride, and alkali metal carbonates, such as for example, potassium carbonate. The reaction is conveniently effected in a suitable organic solvent, such as an ether, for example, tetrahydrofuran.

Compounds of formula (III) may be prepared by reaction of intermediates of formula (V) with intermediates of formula (VI):

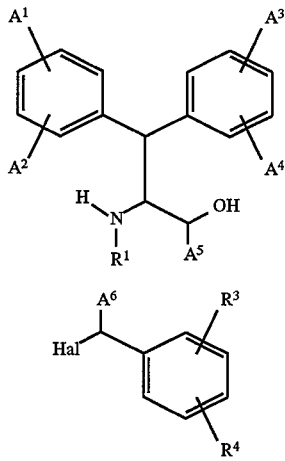

(V)

(VI)

wherein $R^1$, $R^3$, $R^4$, $A^1$, $R^{15}$, $A^2$, $A^3$, $A^4$, $A^5$, and $A^6$ and Hal are as previously defined, in the presence of a base.

Suitable bases of use in the reaction include alkali or alkaline earth metal hydrides, for example, sodium hydride.

The reaction is conveniently carried out in a suitable organic solvent, such as an ether, for example, tetrahydrofuran, suitably at ambient temperature.

Compounds of formula (V) may be prepared from the corresponding compounds of formula (VII)

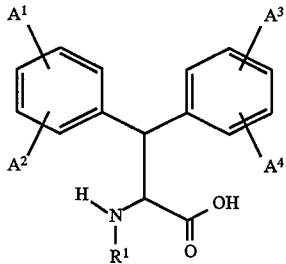

(VII)

wherein $R^1$, $A^1$, $A^2$, $A^3$, and $A^4$ is as previously defined by using conventional methods.

Suitable reducing agents include metal hydrides, such as lithium aluminium hydride. The reaction is conveniently effected in a suitable organic solvent, such as an ether, for example, tetrahydrofuran, suitably at elevated temperature, such as the reflux temperature of the solvent.

Intermediates of formula (VII) wherein $R^1$ is H may be prepared from the intermediate of formula (VIII)

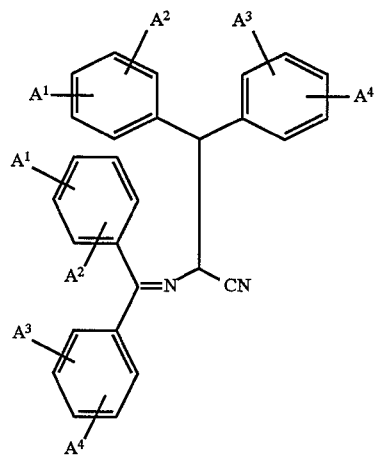

(VIII)

by hydrolysis.

The reaction is conveniently effected by heating a solution of the compound of formula (VIII) in concentrated hydrochloric acid at reflux.

The compound of formula (VIII) may be prepared by reaction of the compound of formula (IX) with a compound of formula (X):

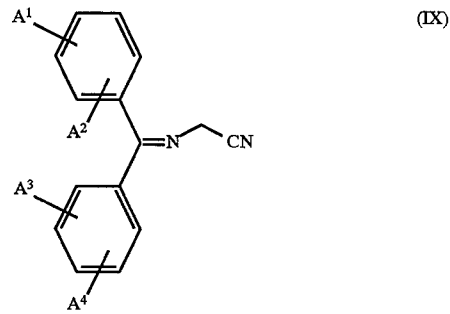

(IX)

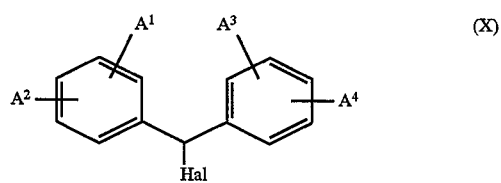

(X)

wherein Hal is as previously defined, in the presence of a base.

Suitable bases of use in the reaction include metal hydroxides, for example, sodium hydroxide. The reaction is conveniently effected in a mixture of water and a suitable organic solvent, such as a hydrocarbon, for example, toluene, in the presence of a phase transfer catalyst, such as benzyltrimethyl ammonium chloride.

The compound of formula (IX) is commercially available.

Compounds of formula (X) may be prepared according to the procedure described by E. J. Corey, *Tetrahedron Lett.*, 1972, 4339, or by other conventional procedures which will be readily apparent to those skilled in the art.

It will be apparent to those skilled in the art that compounds of formula (I), (II), (III), (V) or (VII) wherein $R^1$ is other than H may be prepared from the corresponding compounds wherein $R^1$ is H by reaction with an alkylating agent, for example, a halide of formula $R^1$-Hal, under conventional conditions.

Compounds of formulae (IV) and (VI) are commercially available or may be prepared by conventional procedures well known to those skilled in the art.

Where the above-described process for the preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The novel compounds may also be resolved by formation of diastereomeric esters or amides, for example, leucine methyl esters, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wutts, *Protective Groups in Organic Synthesis*, John Wiley & Sons, 1991. The protecting groups may be removed at a convenient subsequent stage using methods known from the art.

The following Examples illustrate the preparation of compounds according to the invention.

EXAMPLE 1

(S)-N-(1-((3,5-Bis(trifluoromethyl)phenyl) methyloxy)-3,3-diphenylprop-2-yl)-N-methylglycine a) To a solution of diphenylmethyleneiminoacetonitrile (44 g, 0.20 mol), benzyltrimethyl ammonium chloride (4.4 g, 0.024 mol) and sodium hydroxide (48.4 g, 1.21 mol) in toluene (40 ml) and water (90 ml) was added bromodiphenylmethane (149 g, 0.60 mol) at 0° C. After the solution had been stirred at room temperature for 5 h a mixture of water (200 ml), ethyl acetate (40 ml) and hexane (160 ml) was added. The solution was filtered and the residue washed with ethyl acetate/hexane and dried in vacuo to give 3,3-diphenyl-2-diphenylmethyleneimino)propionitrile 47.6 g. $^1$H NMR (360 MHz, CDCl$_3$) δ7.5–6.87 (20H, m, aryl), 4.8 (1H, d, J=8.85 Hz), 4.69 (1H, d, J=9.2 Hz). An analytical sample was recrystallised from ethyl acetate/hexane mp=152°–153° C.

b) 3,3-Diphenyl-2-(diphenylmethyleneimino) proprionitrile (Example 1 a, 46.7 g, 0.12 mol) was heated in a solution of 5.5M-hydrochloric acid (200 ml) at reflux for 48 h. The solid which crystallised from the cooled solution was removed by filtration, washed with diethyl ether and dried to give β,β-diphenylalanine hydrochloride 21 g. $^1$H NMR (250 MHz, DMSO d$_6$) δ8.6 (3H, vbs), 7.6–7.1 (10H, m), 4.8 (1H, d, J=10.4 Hz), 4.4 (1H, d, J=10.4 Hz).

c) A solution of β,β-diphenylalanine hydrochloride (2.5 g, 9.01 mmol), di-t-butyldicarbonate (3.0 g, 14.02 mmol) and triethylamine (2.6 ml) in dichloromethane (50 ml) was heated at reflux for 0.5 h. To the solution was added N,N-dimethylethylenediamine (0.49 ml) and the solution allowed to cool to room temperature. To the solution was added aqueous citric acid and the organic phase was washed with water, saturated brine and dried (MgSO$_4$). To the residue, obtained after removal of the solvent in vacuo, was added diethyl ether (30 ml) and dicyclohexylamine (1.63 g), to give after filtering and drying N-t-butoxycarbonyl-β,β-diphenylalanine dicyclohexylamine salt, 4.7 g mp 154°–154.5° C. $^1$H NMR, (250 MHz, CDCl$_3$) δ7.4–7.0 (10H, m), 5.0 (1H, d, J=9.5 Hz), 4.7 (1H, dd), 4.5 (1H, d, J=7.05 Hz), 2.8 (2H, m), 1.9–1.5 (10H, m), 1.4–1.0 (19H, m), m/z (CI$^{31}$) 340 (M−H).

d) 2-t-Butoxycarbonyl-β,β-diphenylalanine dicyclohexylamine salt (Example 1c, 75.4 g, 0.144 mol) was liberated from its dicyclohexylamine salt by extraction in ethyl acetate from an aqueous citric acid solution, followed by washing (water and saturated brine) and drying (MgSO$_4$). The solvent was removed in vacuo to give a crystalline mass of the free acid. This solid was dissolved in dimethylformamide (200 ml) and to this solution, cooled to 0.° C., was added 1-hydroxybenzotriazole (26.4 g) and 1-(3-dimethylaminopropyl)-3-ethylcarbodiimide hydrochloride (33.1 g). After stirring the solution at 0° C. for 30 minutes a solution of L-leucine methyl ester hydrochloride (31.4 g) and triethylamine (24.0 ml) in dimethylformamide (50 ml) was added. The solution was stirred at room temperature for 16 h and then ethyl acetate (500 ml) and 10% aqueous citric acid (500 ml) were added. The organic phase was washed successively with 10% citric acid, 10% aqueous sodium carbonate, water, saturated brine and dried (MgSO$_4$). The solvent was removed in vacuo to give N-t-butyloxycarbonyl-diphenylalanyl-L-leucine methyl ester as a mixture of diastereomers (approximately 1:1). To the above solid was added anhydrous trifluoroacetic acid (100 ml). After a total of 30 minutes the solvent was removed in vacuo and a solution of the residue in ethyl acetate was washed successively with 10% aqueous carbonate, saturated brine and dried (MgSO$_4$). The solvent was removed in vacuo and upon addition of ethyl acetate/hexane (1:1) a crystalline solid, 19.63 g was formed. After removal by filtration, and recrystallisation from ethyl acetate/hexane (1:1) this gave a pure sample of D-β,β-diphenylalanyl-L-leucine methyl ester, 12.14 g.

The combined mothor liquors were evaporated to dryness and applied to a column containing silica gel. Elution with ethyl acetate/hexane (1:1) gave pure L-β,β-diphenylalanyl-L-leucine methyl ester 22.68 g as an oil.

e) L-β,β-Diphenylalanyl-L-leucine methyl ester (Example 1 d, 22.5 g) was heated in a solution of 5.5M-hydrochloric add (200 ml) at 140° C. for 24 h under an atmosphere of nitrogen. The suspension was cooled to room temperature and the solid removed by filtration and dried to give L-β,β-diphenylalanine hydrochloride, 12.42 g with an enantiomeric purity >99.0% (as determined by hplc after derivatization by (+)-9-fluorenylethylchloroformate).

f) To a solution of 1M-lithium aluminium hydride in diethyl ether (40 ml, 0.04 mol) was added L-β,β-diphenylalanine hydrochloride (3.70 g, 0.0133 mol, Example 1e) over a period of 1 h. The solution was heated at reflux for 1 h, cooled to room temperature and to the solution was cautiously added 2M-sodium hydroxide (40 ml). After filtering the solution through Celite, the residue was washed with ethyl acetate and the organic phase of the combined filtrates was washed with water, saturated brine and dried (MgSO$_4$). The solid which formed on removal of the solvent in vacuo was washed with hexane to give (S)-2-amino-3,3-diphenylpropan-1-ol 2.52 g. $^1$H NMR(360 MHz, CDCl$_3$) δ7.36–7.14 (10H, m), 3.79 (1H, d, J=10.5 Hz), 3.6 (1H, m), 3.57 (1H, dd, J=10.7 Hz and 3.3 Hz), 3.31 (1H, dd, J=10.7 Hz and 6.7 Hz), m/z (CI$^+$) 228 (M+H).

g) A solution of (S)-2-amino-3,3-diphenylpropan-1-ol (2.3 g, 0.010 mol, Example 1f) and di-t-butyldicarbonate (2.65 g, 0.0122 mol) in dichloromethane (25 ml) was stirred at room temperature for 1 h. The solid which formed on removal of the solvent was recrystallized from diethyl ether to give (S)-2-t-butoxycarbonylamino-3,3-diphenylpropan-1-ol (2.85 g).

$^1$H NMR (250 MHz, CDCl$_3$) δ7.34–7.15 (10H, m), 4.58 (1H, bd), 4.48 (1H, m), 4.1 (1H, d, J=10.6 Hz), 3.67 (1H, dd, J=11.13 Hz and 3.11 Hz), 3.5 (1H, dd, J=11.3 Hz and 4.45 Hz), 1.31 (9H, s).

h) To a cooled solution (0° C.) of (S)-2-t-butoxycarbonylamino-3,3-diphenylpropan-1-ol (2.04 g, 6.2 mmol, Example 1 g) in tetrahydrofuran (50 ml) and dimethylformamide (10 ml) was added sodium hydride (0.187 g, 80% suspension in oil) over 15 minutes. After an additional 10 minutes 3,5-bis(trifluoromethyl)benzyl bromide (1.14 ml) was added and the solution stirred at room temperature for 16 h. The solvent was removed in vacuo and the residue partitioned between CH$_2$Cl$_2$ and water. After washing the organic phase with saturated brine and drying (MgSO$_4$), the solvent was removed in vacuo and the residue chromatographed on silica gel in ethyl acetate/hexane (0:100 to 50:50) to give (S)-2-t-butoxycarbonylamino-1-((3,5bis (trifluoromethyl)phenyl)methyloxy)3,3-diphenylpropane, 2.92 g.

i) A solution of (S)-2-t-butoxycarbonylamino-1-((3,5-bis (trifluoromethyl)phenyl)methyloxy)-3,3diphenylpropane (2.92 g, Example 1h) in trifluoroacetic acid (20 ml) was evaporated after 10 minutes. A solution of the residue in CH$_2$Cl$_2$ was washed with 10% aqueous Na$_2$CO$_3$, water, saturated brine and dried (MgSO$_4$). Removal of the solvent in vacuo gave 2-amino-1((3,5-bis(trifluoromethyl) phenyl) methyloxy)-3,3-diphenylpropane.

j) To a solution of (S)-2-amino-1-((3,5-bis (trifluoromethyl) phenyl)methyloxy)-3,3-diphenylpropane (8.6 g, Example 1i) and anhydrous K$_2$CO$_3$ (13.0 g)in dimethylformamide (50 ml) was added methyl bromoacetate (4.5 ml). The reaction was stirred at room temperature for 0.75 h then diluted with ethyl acetate (200 ml) and washed with water (4×100 ml), brine (100 ml), dried over MgSO$_4$ and evaporated to dryness. The residual oil was purified on silica gel eluting with petroleum ether-ethyl acetate mixtures to give (S)-N-(1-((3,5-bis(trifluoromethyl)phenyl) methyloxy)-3,3-diphenylprop-2-yl)glycine methyl ester as an oil (7.61 g) $^1$H NMR (360 MHz, CDCl$_3$) δ7.77 (1H, s), 7.71 (2H, s), 7.42 (2H, d, J=7.4 Hz), 7.33–7.13 (8H, m), 4.44 (2H, s), 4.12 (1H, d, J=7.2 Hz), 3.73–3.69 (1H, m), 3.63 (3H, s), 3.57–3.52 (1H, m), 3.53 (2H, d, J=6.7 Hz) and 3.44–3.36 (1H, m).

k) To a solution of the product of Example 1j (7.6 g) in anhydrous dimethylformamide (80 ml) was added methyliodide (4.5 ml) and anhydrous potassium carbonate (10.0 g) and the reaction stirred under N$_2$ at room temperature for 16 hrs. The reaction was diluted with ethyl acetate (200 ml) and washed with water (4×100 ml) and brine (100 ml), dried over MgSO$_4$ and evaporated in vacuo. The residue was purified by column chromatography on silica gel eluting with petroleum ether-ethyl acetate mixture to yield (S)-N-(1-((3,5-bis(trifluoromethyl) phenyl)methyloxy)-3,3-diphenylprop-2-yl)-N-methylglycine methyl ester. $^1$H NMR (360 MHz, CDCl$_3$) δ7.76 (1H, s), 7.69 (2H, s), 7.37–7.11 (10H, m), 4.41–4.30 (2H, ABq, J=12.6 Hz), 4.20 (1H, d, J=11.4 Hz), 3.78–3.64 (2H, m), 3.56–3.36 (6H, m) and 2.48 (3H, brs).

l) To a solution of the product of Example 1k (1.5 g) in tetrahydrofuran (30 ml) was added potassium hydroxide (312 mg) in water (10 ml) and heated to reflux for 16 hrs.

After evaporation of the solvent the residue was acidified by addition of hydrogen chloride (2N, 30 ml) and the product extracted into diethyl ether (3×30 ml), dried over magnesium sulphate and evaporated in vacuo. The residue was purified by column chromatography on silica gel eluting with petroleum ether-ethyl acetate and methanol mixtures to yield (S)-N-(1-((3,5-bis(trifluoromethyl)phenyl)methyloxy-3,3-diphenylprop-2-yl) -N-methylglycine. mp 61°–63° C., m/z (CI$^{30}$)=526 (M+H) (CI$^{31}$)=524 (M–H). $^1$H NMR (360 MHz, DMSO) δ7.99 (1H, s), 7.93 (2H, s), 7.49–7.10 (10H, m), 4.53–4.45 (2H, ABq, J=13 Hz), 4.20 (1H, d, J=11.7 Hz), 4.05–4.03 (1H, m), 3.53–3.42 (4H, m) and 2.32 (3H, s).

EXAMPLE 2

(S)-N-(1-(((3-t-Butyl-5-chloro)phenyl)methyloxy)-3,3 diphenylprop-2-yl)-N-methylglycine acetate salt a) 4-t-Butyl-2-chloroaniline (30 g) was dissolved in dichloromethane (1.21) and the solution was cooled to –5° C. N-Chlorosuccinimide (21.7 g) was added portionwise to the vigorously stirred solution and stirring was continued for 1 h. Dimethyl sulfide (36 ml) was added to the solution (–5° C.) and stirring was continued for a further 1 h. The solution was then cooled to –65° C. and triethylamine (27 ml) was added. This solution was evaporated to half volume, washed successively with sodium hydroxide (1N), water and brine. The organic solution was dried (MgSO$_4$) and evaporated in vacuo and the residue was purified on silica using hexane to 3% ether in hexane as eluent. This afforded 4-t-butyl-2-chloro-6-(methylthiomethyl)aniline (31.2 g) as a red oil. $^1$H NMR (250 MHz, CDCl$_3$) δ1.27 (9H, s, (CH$_3$)$_3$, 1.99 (3H, s, SCH$_3$), 3.69 (2H, s, CH$_2$SCH$_3$), 4.38 (2H, brs, NH$_2$), 6.92 (1H, d, J=2.0 Hz, Ar—H), 7.21 (1H, d, J=2.0 Hz, ArH). m/z (CI$^+$)=244 (M$^+$+1, 100%).

b) 4-t-Butyl-2-chloro-6-(methylthiomethyl)aniline (1.3 g) was dissolved in methanol (50 ml) and Raney-nickel (prewashed to pH 7) was added portionwise until t.l.c. indicated all starting material had reacted (ether-hexane, 1:10). The Raney-nickel was removed by filtration through Celite and the filtrate was evaporated. The residue was dissolved in ether and washed with brine, dried (MgSO$_4$) and evaporated. The residue was purified on silica using hexane and 5% ether in hexane as eluent to afford 4-t-butyl-2-chloro-6-methylaniline as a yellow liquid. $^1$H NMR (360 MHz, CDCl$_3$) δ1.26 (9H, s, (CH$_3$)$_3$), 2.19 (3H, s, CH$_3$), 3.97 (2H, s, NH$_2$), 6.97 (1H, d, J=2.0 Hz, ArH), 7.14 (1H, d, J=2.0 Hz, ArH).

c) 4-t-Butyl-2-chloro-6-methylaniline (1.97 g) was dissolved in ethanol (50 ml), sulphuric acid (1.88 ml, conc.) was added dropwise and the resulting blue solution was heated at reflux. Sodium nitrite (1.72 g) was added portionwise over 30 min. The resulting mixture was heated at reflux for a further 30 rain, then cooled and was poured onto ice water and extracted with ether (2×50 ml). The ethereal extract was dried (MgSO$_4$) and evaporated and the residue was purified on silica using hexane as eluent to afford 3-t-butyl-5-chlorotoluene as a colourless oil. $^1$H NMR (360 MHz, CDCl$_3$) δ1.29 (9H, s, (CH$_3$)$_3$), 2.31 (3H, s, CH$_3$), 6.98 (1H, brs, ArH), 7.05 (1H, brs, ArH), 7.15 (1H, brs, ARH). MS (CI$^-$) m/z 181 (M$^+$–H, 100%).

d) 3-t-Butyl-5-chlorotoluene (5.7 g) was dissolved in carbon tetrachloride (80 ml) and N-bromosuccinimide (5.56 g) was added followed by benzoyl peroxide (750 mg). This mixture was heated at reflux for 6 h. The mixture was cooled, filtered through Celite and the filtrate was concentrated in vacuo. The residue was purified by chromatography on silica using hexane as eluent to afford 3-t-butyl-5-chlorobenzyl bromide as a colourless liquid. $^1$H NMR (360 MHz, CDCl$_3$) δ1.31 (9H, s, (CH$_3$)$_3$), 4.42 (2H, s, CH$_2$), 7.20 (1H, t, J=1.5 Hz, ArH), 7.26 (1H, t, J=1.5 Hz, ArH), 7.28 (1H, t, J=1.5 Hz, ArH).

e) To a solution of (S)-2-t-butoxycarbonylamino-3,3-diphenylpropan-1-ol (Example 1 g, 0.964 g) and 3-t-butyl, 5-chlorobenzyl bromide (Example 2d. 0.701 g) in dimethylformamide (2 ml) was added sodium hydride (60% suspension in oil, 0.161 g). After 16 h at room temperature saturated NH$_4$Cl and ethyl acetate (50 ml) were added and the organic phase was washed with saturated brine and dried (MgSO$_4$). After evaporation in vacuo the residue was purified on silica gel (eluting with 0–2% ethyl acetate in petroleum ether) to give (S)-2-butoxycarbonylamino-1-(((3-t-butyl-5-chloro)phenyl)methyloxy)-3,3-diphenylpropane. $^1$H NMR (360 MHz, CDCl$_3$) δ7.3–7.1 (13H, m), 4.77 (1H, d, J=9.66 Hz), 4.6 (1H, bt), 4.40 (1H, d, Jgem=120. Hz), 4.31 (1H, d, J=12.03 Hz), 4.25 (1H, d, J=10.8 Hz), 3.4 (1H, dd, J=9.3, 2.9 Hz), 3.3 (1H, dd, J=9.3, 2.9 Hz), 1.31 (9H, s).

f) To a cooled (0° C.) solution of the product of Example 2e (0.588 g) in tetrahydrofuran (5 ml) and dimethylformamide (1 ml) was added sodium hydride (80% suspension in oil, 0.042 g). After stirring the solution at 0° C. for 0.5 h methyl iodide (0.36 ml) was added and stirred at room temperature for a further 16 h. Water (50 ml) and ethyl acetate (50 ml) were added and the organic phase washed further with water, saturated brine and dried (MgSO$_4$). After evaporation in vacuo the residue was chromatographed on silica gel (eluting with 15% ethyl acetate in petroleum ether bp 60°–80° C.) to give (S)-2-(N-t-butoxycarbonyl-N-methyl)-1-((3-t-butyl-5chloro)phenyl)methyloxy)-3,3-phenylpropane m/z 522, 524 (M+1).

g) The product of Example 2f (0.611 g) was dissolved in 4M HCl in methanol (10 ml). After 1 h the solution was evaporated to dryness and the residue crystallised from ethyl acetate to give (S)-1-(((3-t-butyl-5-chloro )phenyl)methyloxy)-3,3-diphenyl-2-methylaminopropane hydrochloride salt, mp 201°–203° C. $^1$H NMR (360 MHz, DMSO-d$_6$) δ7.57 (2H, d, J=7.38 Hz), 7.39–7.17 (11H, m), 4.5 (1H, bm), 4.46 (1H, d, J=12.3 Hz), 4.3 (1H, d, J=11.6 Hz), 4.32 (1H, d, J=12.2 Hz), 3.67 (1H, dd), 3.35 (1H, dd, J=11.07, 4.31 Hz), 2.46 (3H, s), 1.26 (9H, s).

h) To a solution of the product of Example 2 g (0.46 g) in dimethylformamide (5 ml) was added anhydrous K$_2$CO$_3$ (0.31 g) and methyl bromoacetate (0.050 ml). After stirring the solution for 4 h at room temperature, water (50 ml) and ethyl acetate (50 ml) were added and the organic phase washed with saturated brine and dried (MgSO$_4$). After evaporation in vacuo the residue was chromatographed on silica gel (eluting with ethyl acetate:hexane (1:5) to give (S)-N-(1-(((3-t-butyl-5chloro)phenyl)methyloxy)-3,3-diphenylprop-2-yl)-N-methylglycine methyl ester m/z (CI$^{30}$)=494, 496(M+H). $^1$H NMR 4.20 (1H, d, J=10.8 Hz), 4.15 (1H, d, J=12.0 Hz), 3.7 (1H, m), 3.60 (1H, dd, J=9.93, 2.11 Hz), 3.51 (3H, s), 3.49 (1H, d, J=16.7 Hz), 3.35 (1H, d, J=16.7 Hz), 3.34 (1H, dd, J=9.90, 5.57 Hz).

i) To a solution of the product of Example 2 h (0.12 g) in methanol (10 ml) was added 4M-NaOH (5 ml). The solution was stirred at room temperature for 1 h then methanol (10 ml) added and the solution heated to boiling (for 2 minutes). To the cooled solution was added acetic acid (1 ml), ethyl acetate (20 ml) and saturated brine (20 ml). The organic phase was dried (MgSO$_4$) evaporated in vacuo and the residue chromatographed on silica gel (eluting with a gradient of chloroform to chloroform:methanol:acetic acid (85:10:5 ). The fractions containing the product were evaporated to a small volume then freeze dried from glacial acetic acid to give (S)-N-(1-(((3-t-butyl-5-chloro)phenyl)methyloxy)-3,3-diphenylprop-2-yl)-N-methylglycine acetate salt m/z (CI$^+$) 480, 482 (M+H). $^1$H NMR (360 MHz, DMSO-d$_6$) 7.48 (2H, d, J=7.16 Hz), 7.41 (2H, d, J=7.15 Hz), 7.3–7.1 (9H, m), 4.34 (1H, d, J=12.4 Hz), 4.25 (1H, d, J=12.3 Hz), 4.17 (1H, d, J=11.7 Hz), 4.01 (1H, m), 3.4 (2H, m), 3.33 (2H, s), 2.30 (3H, s), 1.90 (3H, s), 1.26 (9H, s).

The following examples were prepared by a method analogous to that described in Example 2 using the appropriate benzyl bromide.

EXAMPLE 3

(S)-N-(1-((3,5-Dimethylphenyl)methyloxy)-3,3-diphenylprop-2-yl)-N-methylglycine mp=124°–27° C., m/z (CI$^+$)=418 (M+H) $^1$H NMR (360 MHz, DMSO-d$_6$) δ7.48 (2H, d, J=7.2 Hz), 7.41 (2H, d, J=7.2 Hz), 7.26–7.09 (6H, m), 6.67 (1H, s), 6.80 (2H, s), 4.27 (1H, d, J=12.7 Hz), 4.18–4.15 (2H, ABq, J=6.3 Hz), 4.03–3.85 (1H, m), 3.44–3.26 (4H, m), 2.29 (3H, s) and 2.22 (6H, s).

EXAMPLE 4

(S)-N-(1-(((3-chloro-5-methyl)phenyl)methyloxy)-3,3-diphenylprop-2-yl)-N-methylglycine m.p.=52°–54° C., $^1$H NMR (360 MHz, DMSO-D$_6$) δ7.48 (2H, d, 7.41 (2H, d, J=7.3 Hz), 7.23 (4H, ddd, J=2.4, 7.3, (4H, m), 6.98 (1H, s), 4.31 (1H, d, J=12.4 Hz), 4.20 7.8, 12.4 Hz), 4.00 (1H, m), 3.44–3.28 (4H, m), 2.30 (3H, s). m/z (CI$^+$)=438 ($^{35}$Cl, M+H), 440 ($^{37}$Cl, M+H).

EXAMPLE 5

(S)-N-(1-((3-bromo-5-methyl)phenyl)methyloxy)-3,3-diphenylprop-2")-N-methylglycine m.p.=87°–90° C., $^1$H NMR (360 MHz, DMSO-D$_6$, 353° K.) δ7.42 (2H, d, J=7.3 Hz), 7.32 (2H, d, J=7.3 Hz), 7.25 (1H, s), 7.19 (5H, ddd, J=1.6, 7.3, 8.7 Hz), 7.10 (2H, app.t, J=7.3 Hz), 6.95 (1H, s), 4.25 (2H, br s), 4.16 (1H, d, J=11.0 Hz), 3.89 (1H, m), 3.37 (2H, br d, J=4.4 Hz), 3.13 (2H, br, m), 2.24 (6H, s). m/z (CI$^+$) 482 ($^{79}$Br, M+H), 484 ($^{81}$Br, M+H).

EXAMPLE 6

(S)-N-(1-((3,5-dichlorophenyl)methyloxy)-3,3-diphenylprop-2-yl)-N-methyl glycine hydrochloride salt $^1$H NMR (360 MHz, DMSO-D$_6$) δ7.65 (3H, d, J=7.4 Hz), 7.51–7.17 (10H, m), 4.86–4.82 (1H, m), 4.61 (1H, d, J=11.7 Hz), 4.42–4.28 (2H, ABq, J=12.6 Hz), 4.20–4.14 (1H, m), 3.88 (1H, d, J=17.1 Hz), 3.70–3.61 (2H, m) and 2.81 (3H, s). m/z (CI$^+$)=458 (M+H), mp=156°–159° C.

EXAMPLE 7

(S)-N-(1-(((3-methyl-5-vinyl)phenyl)methyloxy)-3.3-diphenylprop-2-yl)-N-methylglycine a) A solution of (S)-N-(1-(((3-bromo-5 methyl)phenyl)methyloxy)-3,3-diphenylprop-2-yl)-N methylglycine (Example 5, 0.8 g, 1.7 mmol) and vinyl tributyl tin (0.54 ml, 1.83 mmol) in dry toluene (6 ml) was degassed (N$_2$) for 10 min, then tetrakis(triphenylphosphine)palladium (0) (0.04 g, 0.003 mmol) was added and the mixture heated at reflux under N$_2$. After 3 h a further 0.04 g of tetrakis (triphenylphosphine) palladium (0) was added and reflux continued for 16 h. The reaction mixture was cooled to room temperature, the solvent was evaporated in vacuo and the residue purified by chromatography on silica gel (hexanes-ethyl acetate 97:3 then 9:1 then 4:1) to provide (S)-N-(1-(((3-methyl-5-vinyl)phenyl) methyloxy-3,3-diphenylprop-2-yl)-N-methylglycine methyl ester as an oil. $^1$H NMR (250 MHz, CDCl$_3$) δ7.40–7.10 (10H, m), 6.94 (1H, s), 6.70 (1H, dd, J=11.2, 17.6 Hz), 5.74 (1H, d, J=17.6 Hz), 5.24 (1H, d, J=11.2 Hz), 4.36–4.10 (3H, m), 3.76–3.30 (8H, m), 2.46 (3H, br s), 2.34 (3H, s), m/z (CI$^+$) 444 (M+H, 100%).

b) (S)-N-(1-(((3-methyl-5-vinyl)phenyl)methyloxy-3,3-diphenylprop-2-yl)-N-methylglycine methyl ester (Example 7a) was treated with potassium hydroxide as described in Example 1 to provide (S)-N-1-(((3-methyl-5-vinyl)phenyl) methyloxy)-(3,3-diphenylprop-2-yl)-N-methylglycine as a foamy solid, $^1$H NMR (250 MHz, CDCl$_3$) δ7.37–7.14 (10H, m), 7.13 (1H, s), 7.07 (1H, s), 6.92 (1H, s),6.66 (1H, dd, J=11.0, 17.0 Hz), 5.72 (1H, d, J=17.0 Hz), 5.22 (1H, d, J=11.0 Hz), 4.36 (2H, dd, J=11.8 Hz), 4.26 (2H, dd, J=11.8 Hz), 3.99 (1H, d, J=11.8 Hz), 3.72 (1H, m), 3.50–3.16 (8H, m), 2.31 (3H, s), 2.29 (3H, s). m/z (CI$^+$)430 (M+H).

EXAMPLE 8

(S)-N-(1-(((3-ethyl-5-methyl)phenyl)methyloxy)-3,3-diphenylprop-2yl)-N-methylglycine (S)-N-(1-(((3-methyl-5-vinyl)phenyl)methyloxy)-3,3-diphenylprop-2-yl)-N-methylglycine (Example 7) was dissolved in methanol and hydrogenated for 2 h at 40 psi using palladium on activated charcoal (10%) as catalyst. The reaction mixture was filtered through celite and the filtrate concentrated in vacuo to provide the title Compound as an oily solid. $^1$H NMR (250 MHz, CDCl$_3$) δ7.38–7.14 (10H, m), 6.94 (1H, s), 6.87 (2H, s), 4.33 (2H, m), 3.99 (1H, d, J=11.2 Hz), 3.71 (1H, br m), 3.48–3.14 (4H, m), 2.54 (2H, q, J=7.3 Hz), 2.31 (6H, brs), 1.21 (3H, t, J=7.3 Hz). m/z CI$^+$) 432 (M+H).

EXAMPLE 9

(S)-N-(1-((3,5-Bis(trifluoromethyl)phenyl) methyloxy)-3,3-diphenylprop-2-yl)alanine The product of Example 1i was alkylated with methyl DL-2-bromopropionate as described in Example 1j and then saponified as described in Example 11 to give two separated diastereomers as freeze dried solids.

Diastereomer A Found C, 57.17; H, 5.00; N, 2.14: O$_{27}$H$_{25}$F$_6$NO$_3$. 2.25(H$_2$O) requires C, 57.29; H, 5.25; N 2.47%.

$^1$H NMR (360 MHz, DMSO-d$_6$) δ5 8.03 (1H, s), 8.01 (2H, s), 7.55 (2H, d, J=7.74 Hz), 7.38–7.15 (8H, m), 4.63 (1H, d, Jgem=12.9 Hz), 4.51 (2H, m+d, J=12.9 Hz), 4.40 (1H, d, J=11 Hz), 3.79 (1H, q), 3.70 (1H, d), 3.5 (1H, dd), 1.38 (3H, d, J=7.11 Hz). m/z (CI$^+$)=526 (M+H), (CI$^-$)=524 (M–H).

Diastereomer B $^1$H NMR (360 MHz, DMSO-d$_6$) δ8.0 (1H, s), 7.9 (2H, s), 7.41–7.10 (10H, m), 4.60 (1H, (1H, d, Jgem=13.1 Hz), 4.03 (1H, d, J=(1H, dd), 3.16 (1H, dd), 1.00 (3H, d, J=6.8 Hz). m/z (CI$^+$)=526 (M+H), (CI$^-$)=524 (M–H).

EXAMPLE 10

(S)-2-(N,N-bis(carboxymethyl)amino)-1-((3,5-bis (trifluoromethyl)methyloxy)-3,3-diphenylpropane The amine (Example 1i, liberated from the salt by partitioning between ethyl acetate and Na$_2$CO$_3$ solution followed by drying MgSO$_4$ and evaporation, 1.6 g), K$_2$CO$_3$ (1.07 g) methyl bromoacetate (0.7 ml) in dimethylformamide (10 ml) were heated to 100° C. for 2 h. The solution was diluted with ethyl acetate (100 ml)and washed with water, saturated brine and dried (MgSO$_4$). After evaporation in vacuo the residue was purified by silica gel chromatography to give (S)-2-(bis ((carbomethoxy)methyl)amino)-1-((3,5-bis (trifluoromethyl)phenyl)methyloxy-3,3-diphenylpropane as an oil. $^1$H NMR (360 MHz, CDCl$_3$) δ7.78 (1H, s), 7.69 (2H, s), 7.4–7.1 (10H, m), 4.41 (1H, d, J=12.5 Hz), 4.30 (1H, d, J=11.5 Hz), 4.20 (1H, d, J=12.5 Hz), 3.86 (1H, m), 3.7 (1H, d, J=17.5 Hz), 3.5 (1H, d, J=17.5 Hz), 3.5 (6H, s), 3.4 (1H, m). A solution of this oil (0.5 g) in tetrahydrofuran (20 ml) was treated with KOH (0.234 g) in water (5 ml) and the solution heated to reflux for 16 h. The solution was concentrated in vacuo and on acidification to pH 2 with 6N-HCl gave the title compound as a solid. $^1$H NMR (DMSO-d$_6$) δ7.99 (1H, s), 7.94 (2H, s), 7.51 (2H, d, J=7.38), 7.44 (2H, d, J=7.31), 7.26–7.11 (6H, m), 4.55 (1H, d, Jgem=12.9 Hz), 4.38 (1H, d, Jgem=12.9 Hz), 4.28 (1H, d, J=11.6 Hz), 4.07 (1H, m), 3.46 (4H, dd, Jgem=18.1 Hz). m/z (FAB$^+$) 570 (M+H), (FAB$^-$) 568 (M–H).

EXAMPLE 11

(S)-N-(1-(((3-methoxy-5-methyl)phenyl)methyloxy) -3,3-diphenylprop-2-yl)-N-methylglycine a) A refluxing solution of 3,5-dimethylanisole (13 g), azoisobutyronitrile (1.6 g) and N-bromosuccinimide (17 g) in carbon tetrachloride (100 ml) was irradiated with light for 6 h. The solution was filtered and the solvent removed in vacuo. The residue was purified by chromatography on silica gel (eluting with 0–5% ethyl acetate—petroleum ether bp=60°–80° C.) to yield 3-bromomethyl-5-methylanisole.

b) The product of Example 11a was used to prepare the title compound by a method analogous to that described in Example 2. $^1$H NMR (250 MHz, CDCl3) δ7.42–7.20 (10H, m), 6.66(1H,s), 6.62(2H,s), 4.35(1H,d, Jgem=11.6 Hz),4.24 (1H,d, J$_{gem}$=11.7 Hz), 4.42–4.08(2H,m),3.79(3H,s), 3.64 (1H,dd), 3.55(2H,s) 3.41(1H, dd, J=11.1, 6.5 Hz) 2.5(3H,s), 2.32(3H,s). $^1$H NMR (25 MHz, DMSO d$_6$) δ7.49 (2H,d J=7.11 Hz), 7.42(2H,d J=7.12 Hz), 7.26(6H,m), 6.63(2H,s), 6.60(1H,s), 4.31(1H, d, Jgem=12.1 Hz), 4.19(1H, d, J=11.8 Hz), 4.16(1H, d, J$_{gem}$=12.1 Hz), 4.04(1H,m), 3.71(3H,s), 3.44–3.30(4H,m), 2.30(3H,s), 2.24(3H,s). m/z (CI$^+$)=434 (M+H)

EXAMPLE 12

(S)-N-(1-((3,5-bis(trifluoromethyl)phenyl) methyloxy)-3,3-diphenylprop-2-yl)-N-ethylglycine Ethyl iodide was used instead of methyl iodide to prepare the title compound by a method analogous to that described in Example 2. $^1$H NMR (250 MHz, DMSO d6) δ8.02(1H, s), 7.94(2H, s), 7.53 (2H, d, J=7.1 Hz), 7.46 (2H, d, J=7.1 Hz), 7.31–7.10(6H,m), 4.56–4.45(2H, ABq, J=12.8 Hz), J=7.0 Hz). 4.42–4.36 (2H, m), 3.70–3.51(4H, m), 0.84(3H, t, J=7.0 Hz).

EXAMPLE 13

(R)-N-(1-((3,5-Bis(trifluoromethyl)phenyl) methyloxy)-3,3-diphenylprop-2yl)-N-methylglycine The title compound was prepared as described in Example 1 using D-β, β-diphenylalanyl-L-leucine methyl ester (Example 1d) which after hydrolysis in a similar manner to that described in Example 1e gave D-β, β-diphenylalanine hydrochloride. Using the procedures described in Examples 1f-1 D-β,β-diphenylalanine hydrochloride was converted to the title compound m/z (CI$^+$)=526 (M+H). $^1$H NMR identical to the product of Example 1. Chiral hplc (Chiral AGP, 10% MeCN in 10 mM K$_2$HPO$_4$ pH6.5) >99% enantiomeric excess.

EXAMPLE 14

N-(3-((3,5-Bis(trifluoromethyl)phenyl)methyloxy)-1,1-diphenylbut-2-yl)-N-methylglycine a) To a cooled (−30° C.) solution of N-t-butoxycarbonyl-β, β-diphenylalanine (13.8 g) and triethylamine (28 ml)in dimethylformamide (200 ml) was added isobutylchloroformate (3.12 ml) such that the temperature remained below −20° C. After 15min a solution of N,O-dimethylhydroxylamine hydrochloride (13 g) in CH$_2$Cl$_2$ was added. The solution was stirred at room temperature for 18 h whereupon it was diluted with ethyl acetate and washed successively with 10% aqueous citric acid, water, saturated NaHCO$_3$, saturated brine, and dried (MgSO$_4$). Removal of the solvent in vacuo gave N-t-butoxycarbonyl-β, β-diphenylalaninyl-(N-methoxy,N-methyl)amide which was used without further purification. To a cooled (−10° C.) solution of N-t-butoxycarbonyl-β, β-diphenylalaninyl-(N-methoxy,N-methyl) amide (5 g) in tetrahydrofuran (130 ml) was added 1M-methylmagnesium chloride (13 ml). The solution was stirred for 2 h whereupon it was diluted with diethyl ether and a saturated solution of ammonium chloride was added. The organic phase was washed with water, saturated brine and dried (MgSO$_4$). The residue was chromatographed on silica (eluting with ethyl acetate/petroleum ether b.p. 60°–80° C. 10%,20%,30%) to give 2-N-t-butoxycarbonylamino-1,1-diphenylbutan-3-one, $^1$H NMR (CDCl$_3$,250 MHz) δ7.46–7.12 (10H,m,Ph), 4.94(1H,dd,J=8.7, 11.6 Hz), 4.26(1H,d,J=11.7 Hz), 1.91(3H,s), 1.27(9H,s).

b) To a solution of 2-N-t-butoxycarbonylamino-1,1-diphenylbutan-3-one (2.74 g, Example 14a) in methanol (100 ml) was added sodium borohydride (0.73 g). After 4 h the solution was diluted with ethyl acetate and washed with dilute HCl, water, saturated brine, and dried (MgSO$_4$). Removal of the solvent in vacuo gave 2-N-t-butoxycarbonylamino-1,1-diphenyl-3-hydroxybutane as a mixture of diastereoisomers (3:1). To a solution of the mixture of diastereoisomers (2.15 g) and 3,5-bis (trifluoromethyl) benzyl bromide (1.8 ml)in dimethylformamide (20 ml) was added sodium hydride (0.304 g, 60% suspension in oil). After 18 h the reaction was quenched by addition of saturated ammonium chloride and the product extracted into ethyl acetate. The organic phase was washed with water (twice), saturated brine, and dried (MgSO$_4$). After removal of the solvent in vacuo the residue was purified by chromatography on silica (eluting with ethyl acetate/petroleum ether b.p. 60°–80° C., 2%, 5%) to give 2-N-t-butoxycarbonylamino-1,1-diphenyl-3-((3,5-is (trifluoromethyl)phenyl)methyloxy)butane as a mixture of diastereomers (2:1).

c) A solution of 2-N-t-butoxycarbonylamino-1,1-diphenyl-3-((3,5-bis(trifluoromethyl)phenyl)methyloxy) butane (Example 14b, 1g) in dimethylformamide (5 ml) was alkylated and deprotected in an analogous manner to that described in Example 2f,2g,2h,2i to give N-(3-((3,5-bis (trifluoromethyl) phenyl)methyloxy)-1,1-diphenylbut-2-yl)-N-methylglycine as a mixture of diastereoisomers which were separated by chromatography on silica (eluting with methanol in CH$_2$Cl$_2$ 0%,5%).

Diasteroisomer A: $^1$H NMR (CDCl$_3$ 250 MHz) δ1.36(3H, d,J=5.7 Hz), 2.51(3H,s), 3.32–3.45(2 h,ABq, J=18 Hz), 3.63(1H,dd,J=11 Hz), 3.68(1H,dq),3.86(1H,d,J=12 Hz), 4.38 (1H,d,j=12 Hz), 438(1H,d J=11 Hz), 4.51(1H,d,J=12 Hz), 7.16–7.43(10H,m),7.71(2H,s), 7.84(1H,s).CHN analysis found C,62.36; H,5.05; N,2.61. C$_{28}$H$_{27}$NO$_3$F$_6$ requires C,62.34; H, 5.05; N, 2.60%.

Diasteroisomer B:$^1$H NMR (CDCl$_3$ $_{250}$ MHz) δ1.10(3H, d,J=6.9 Hz), 2.44(3H,s), 3.26(1H,d, J=16 Hz), 2.52(1H, d, J=16 Hz), 3.68(1H,dq),3.92(1H,dd,J=12.5 Hz), 4.20(1H,d, J=12.5 Hz), 4.52–4.65(2H,ABq, J=12.5 Hz), 7.10–7.44 (10H,m),7.74(2H,s),7.82(1H,s).CHN analysis found C,61.85; H,4.98; N,2.56. C$_{28}$H$_{27}$NO$_3$F$_6$ .0.25(H$_2$O)requires C,61.82; H, 5.10; N, 2.57%.

We claim:

1. A compound of formula (I) as a pharmaceutically acceptable salt or prodrug thereof:

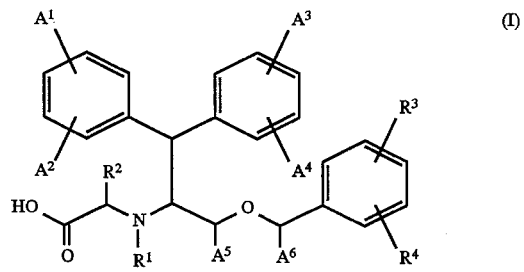

wherein

R$^1$ represents H, C$_{1-4}$alkyl or CH$_2$COOH;

R$^2$ represents H or C$_{1-4}$alkyl, with the proviso that R$^1$ and R$^2$ are not both H;

R$^3$ and R$^4$ each independently represent H, C$_{1-6}$alkyl, C$_{2-6}$alkenyl, C$_{1-6}$alkoxy, halo or trifluoromethyl;

A$^1$, A$^2$ A$^3$ and A$^4$ each independently represent H, C$_{1-6}$ alkyl, C$_{1-6}$ alkenyl, C$_{1-6}$ alkoxy, halo or trifluoromethyl; and A$^5$ and A$^6$ each independently represent H or C$_{1-4}$alkyl.

2. A compound according to claim 1 wherein A$^1$, A$^2$, A$^3$, A$^4$, A$^5$ and A$^6$ are each hydrogen.

3. A compound according to claim 2 where R$^2$ is hydrogen or methyl.

4. A compound according to claim 1 wherein R$^3$ and R$^4$ are located at the 3- and 5- positions of the phenyl ring.

5. A compound of the formula (IA) or a pharmaceutically acceptable salt thereof:

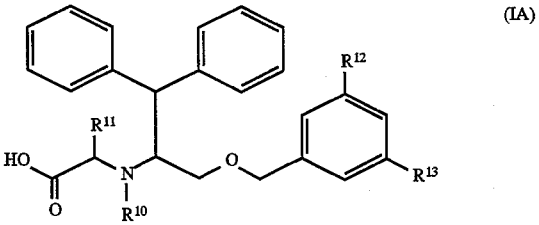

wherein

R$^{10}$ represents H, methyl or CH$_2$COOH;

R$^{11}$ represents H, methyl or ethyl, with the proviso that when R$^{10}$ is H, R$^{11}$ is not H; and $R^{12}$ and $R^{13}$ each independently represent $C_{1-6}$alkyl, $C_{2-6}$alkenyl, $C_{1-6}$alkoxy, halo, or trifluoromethyl.

6. A compound selected from:

(S)-N-(1-((3,5-bis(trifluoromethyl)phenyl)methyloxy)-3,3-diphenylprop-2-yl)-N-methylglycine;

(S)-N-(1-(((3-t-butyl-5-chloro)phenyl)methyloxy)-3,3-diphenylprop-2-yl)-N-methylglycine;

(S)-N-(1-((3,5-dimethyl)phenyl)methyloxy)-3,3-diphenylprop-2-yl)-N-methylglycine;

(S)-N-(1-(((3-chloro-5-methyl)phenyl)methyloxy)-3,3-diphenylprop-2-yl)-N-methylglycine;

(S)-N-(1-(((3-bromo-5-methyl)phenyl)methyloxy)-3,3-diphenylprop-2-yl)-N-methylglycine;

(S)-N-(1-(((3,5-dichlorophenyl)methyloxy)-3,3-diphenylprop-2-yl)-N-methylglycine;

(S)-N-(1-(((3-methyl-5-vinyl)phenyl)methyloxy)-3,3-diphenylprop-2-yl)-N-methylglycine;

(S)-N-(1-(((3-ethyl-5-methyl)phenyl)methyloxy)-3,3-diphenylprop-2-yl)-N-methylglycine;

(S)-N-(1-((3,5-bis(trifluoromethyl)phenyl)methyloxy)-3,3-diphenylprop-2-yl) alanine;

(S)-2-(N,N-bis(carboxymethyl)amino)-1-((3,5-bis(trifluoromethyl)phenyl)methyloxy)-3,3diphenylpropane;

(S)-N-(1-(((3-methoxy-5-methyl)phenyl)methyloxy)-3,3-diphenylprop-2-yl)-N-methylglycine;

(S)-N-(1-((3,5-bis(trifluoromethyl)phenyl)methyloxy)-3,3-diphenylprop-2-yl)-N-ethylglycine; and pharmaceutically acceptable salts thereof.

7. A pharmaceutical compositions comprising one or more compounds of formula (I), or salts or prodrugs thereof, in association with a pharmaceutically acceptable carrier.

8. A method for the treatment of pain, nociception, inflammation, neuropathy, diabetic neuropathy, chemotherapy-induced neuropathy, postherpetic neuralgia, asthma, osteoarthritis, rheumatoid arthritis and migraine, which method comprises administration to a patient in need thereof of a tachykinin-reducing amount of a compound according to claim 1.

* * * * *